United States Patent [19]

Cowfer et al.

[11] 4,339,620

[45] Jul. 13, 1982

[54] COPPER-CATALYZED FLUID-BED ETHYLENE OXHYDROCHLORINATION PROCESS

[75] Inventors: Joseph A. Cowfer, Medina; Jamal S. Eden, Akron; Angelo J. Magistro, Brecksville, all of Ohio

[73] Assignee: The B. F. Goodrich Company, Akron, Ohio

[21] Appl. No.: 239,806

[22] Filed: Mar. 2, 1981

Related U.S. Application Data

[63] Continuation of Ser. No. 91,289, Nov. 5, 1979, abandoned.

[51] Int. Cl.$^3$ .............................................. C07C 17/15
[52] U.S. Cl. ...................................................... 570/243
[58] Field of Search ........................................... 570/243

[56] References Cited

U.S. PATENT DOCUMENTS

| | | | |
|---|---|---|---|
| 2,547,928 | 4/1951 | Davis et al. | 423/502 |
| 2,746,844 | 5/1956 | Johnson et al. | 423/502 |
| 3,232,889 | 2/1966 | Bellis | 260/609 A |
| 3,488,398 | 1/1970 | Harpring et al. | 260/609 A |
| 4,000,205 | 12/1976 | Campbell | 260/654 A |

FOREIGN PATENT DOCUMENTS

7016124  5/1971  Netherlands ............... 260/659 A

OTHER PUBLICATIONS

"Chlorination of Methane with Copper Chloride Melts", Fontana et al–Industrial and Engineering Chemistry, vol. 44, No. 2, pp. 363–368, (Feb. 1952).

"Kinetics and Mechanism of the Catalytic Oxidation of Hydrogen Chloride", Shakhovtseva et al–Translated from Russian, Kinetika i Kataliz, vol. 11, No. 6, pp. 1469–1475, (Nov./Dec. 1970).

*Primary Examiner*—Thomas A. Waltz
*Attorney, Agent, or Firm*—Ernest K. Bean; J. Hughes Powell, Jr.; Alan A. Csontos

[57] ABSTRACT

There is disclosed a method and composition for improving the fluidization characteristics and alleviating or inhibiting stickiness in a supported cupric chloride catalyst used as fluid bed catalyst in oxyhydrochlorinations reactions. The method involves the in situ preparation of the supported cupric chloride catalyst by addition of bare support on which no cupric chloride is deposited to the supported cupric chloride catalyst in the fluidized bed, or the use in the bed as the initial charge or as addition to the bed as makeup, of a composition which is a mixture of supported cupric chloride catalyst and bare support. In either event, as the oxyhydrochlorination proceeds, a portion of the cupric chloride on the supported catalyst becomes released therefrom and deposited in situ on the bare support, and stickiness of the cupric chloride containing catalyst particles to one another in the fluid bed is alleviated or inhibited.

4 Claims, No Drawings

COPPER-CATALYZED FLUID-BED ETHYLENE OXHYDROCHLORINATION PROCESS

This is a continuation of application Ser. No. 091,289, filed Nov. 5, 1979, now abandoned.

BACKGROUND OF THE INVENTION

This invention pertains to fluid bed catalytic oxyhydrochlorination of ethylene to produce 1,2-dichloroethane, commonly called ethylene dichloride (EDC). It relates specifically to a novel method for improving the fluidized copper catalyst used in such oxyhydrochlorination.

EDC is most easily produced commercially by the direct chlorination of ethylene, and is used in greatest quantity for pyrolysis, or "cracking", to produce vinyl chloride monomer (VCM), on which the vinyl plastic industry depends. The pyrolysis reaction produces, in addition to VCM, by-product hydrogen chloride (HCl) which is advantageously utilized at the plant site to produce more EDC for the pyrolysis. This is accomplished by the process called ethylene oxyhydrochlorination (or sometimes, more simply "oxychlorination") which involves the reaction of HCl with oxygen, supplied as such or as air, and ethylene in accordance with the empirical equation:

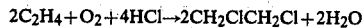

$$2C_2H_4 + O_2 + 4HCl \rightarrow 2CH_2ClCH_2Cl + 2H_2O$$

The ethylene oxychlorination is carried out in many highly successful commercial installations through the world by passing the gaseous reactants at elevated temperature and pressure through a fluidized solid catalyst bed in the manner and under the conditions generally described in Harpring et al U.S. Pat. No. 3,488,398, the disclosure of which is incorporated by reference thereto, as if fully set forth herein. As taught by the Harpring et al patent, in order to achieve sufficient utilization of HCl for formation of EDC, the molar ratio of ethylene to oxygen to HCl is to be maintained in the range of about 1.0 to about 1.2 moles ethylene to about 0.55 to 0.9 moles oxygen for each two moles of HCl, with the most preferred ratio of ethylene to oxygen to HCl being about 1.0 to 0.8/2.0. The process is operated at a temperature in the range of about 190° to 250° C., preferably under a pressure of 10–50 psig, which provides a contact time of from about 10 to about 40 seconds. The reactants are fed into the reactor in a dry state and the pressure-temperature relationships are such that the dew point temperature is always exceeded and there is complete lack of liquid in the reactor. Not more than 0.5% of the catalyst bed is removed from the reactor as fines in a 24 hour period.

The nature of the fluidized catalyst bed is of importance to the success of the ethylene oxyhydrochlorination process. The catalyst bed consists essentially of a copper compound, preferably cupric chloride, uniformly distributed or carried on a fluidizable support, which is a particulate material of the proper ratio of particle sizes, surface area, porosity, density, resistant to attrition and other characteristics to provide proper fluidization and isothermal conditions in the reactor bed, to permit adequate contact between the copper catalyst and the gaseous reactants as they pass through the bed, and to minimize loss of catalyst through passage of fine particles from the reactor with the effluent gases. The fluidizable support, as taught by the Harpring et al patent, is composed of alumina, most desirably activated alumina or microgel alumina since such supports exhibit superior resistance to attrition and ability to fluidize and can be readily prepared to have the desired surface area and ratio of particle sizes in accordance with the "Bayer process" or other bauxite calcination techniques well known to the art. Preparation of the copper catalyst on the fluidizable support is well known to the art, and is described in the referenced Harpring et al patent. Typically cupric chloride is dissolved in water, and the solution is slowly sprayed on the support with continuous mixing (or alternatively adding the support to the solution with mixing) followed by drying the wet subject until it is free flowing, calcining for a few hours at a temperature of about 110° C., and screening to eliminate large particles. The supported catalyst is then ready for addition to the oxyhydrochlorination reactor to function as the fluidized catalyst bed. The supported catalyst is prepared to contain from about 2 to 10 percent by weight copper. It is customarily supplied to the operator of the ethylene oxyhydrochlorination process for addition to the reactor at "start-up" of the process or as "make-up" when the catalyst bed needs replenishing.

Copper catalysts prepared as above have serviced well as oxyhydrochlorination catalysts. However, all such catalysts exhibit, to a more or less degree, a tendency to agglomerate, a characteristic which is called "stickiness" in the trade. The degree of stickiness of the catalyst is dependent on many factors, including the pressure and temperature of the reaction, the absorptive nature or porosity of the catalyst, the amount and distribution of the copper on the particle surfaces, the ratio of the weight of copper to the surface area of the support, the number of active sites available on the catalyst and the manner and degree of their utilization, the presence of contaminants such as sulfur, as well as upon the quantity and ratios of the gaseous reactants in the fluid bed. A certain degree of stickiness is tolerable, but if the catalyst is so sticky that particles continually agglomerate and are not broken up by movement in the fluidized bed, "hot spots" are developed in the bed at the point of the agglomeration, especially at the bottom of the bed. These hot spots may eventually lead to loss of fluidity or "inversion" and total collapse of the fluidized bed. Even if inversion does not occur, agglomeration of the catalyst can cause plugging of the lower portion or "dip leg" of the cyclone above the reactor (indicated by reference numeral 14 of FIG. 1a of the drawing of Harpring et al U.S. Pat. No. 3,488,398 which cyclones separate the catalyst fines from the effluent gases and retain the catalyst in the bed) with the result that large quantities of the catalyst can be lost and operations disrupted. To a large extent, the stickiness of the copper catalyst can be controlled by efficient operation of the process. However, an effective and practical way to inhibit and/or reduce stickiness of the catalyst during operation would be desirable.

SUMMARY OF THE INVENTION

This invention prevents or substantially inhibits or alleviates stickiness in fluid bed catalysts composed of cupric chloride on a fluidizable alumina support used in the ethylene oxyhydrochlorination process to produce EDC. The invention accomplishes this through the expedient of depositing a substantial portion of the cupric chloride on the fluidizable support while the latter is in the fluidized condition, i.e. with the support particles in movement suspended by a flow of gases at the temperature of the reaction. Hence, instead of preparing the supported cupric chloride catalyst for the fluid bed entirely outside the reactor, as in the prior practice, a substantial portion of it is prepared in situ.

The in situ catalyst preparation is accomplished conveniently in any of several ways through use of bare fluidizable alumina support, it being understood that a "bare" support is one on which nothing is deposited. The bare support can be used in substantial proportion with support on which cupric chloride has already deposited in the usual manner, and the novel mixture then charged to the reactor at start up of the process at the oxyhydrochlorination plant. Further, the bare support can be added during operation of the process at a time when the fluid bed is composed solely of supported cupric chloride catalyst, or thereafter, at intervals as required to provide makeup catalyst or to alleviate stickiness developing in the bed.

When bare fluidizable alumina support is provided to the oxyhydrochlorination reactor and mixed with already supported cupric chloride catalyst, subsequent operation of the reactor results in a rapid release of a portion of the cupric chloride from the supported catalyst, particularly that which is concentrated on the outside surfaces of the support particle, and the cupric chloride, in situ, deposits on or transfers to the particles of the bare support. This is evidenced by a change in color of the mass of the fluidized bed from the speckled appearance characteristic of a mixture of greenish cupric chloride bearing particles and white bare support particles, to a uniform pale greenish color throughout. It is believed that the fluidized condition of the bare support particles under reaction conditions unexpectedly permits the cupric chloride from the supported particles to permeate their pores and be distributed throughout their mass in a more efficient and uniform manner than is possible when the cupric chloride is placed on the support in the usual manner outside the reactor.

In any event, operation of the fluid bed to effect the oxyhydrochlorination reaction after deposit of cupric chloride from supported particles onto on bare support particles in situ, while fluidized, inhibits or reduces the tendency of the catalyst to develop stickiness in the fluidized bed which may otherwise be encountered, and fluidization characteristics of the bed are substantially improved.

DETAILED DESCRIPTION OF INVENTION INCLUDING SPECIFIC EMBODIMENTS

In the practice of the process of this invention, according to one preferred embodiment, the oxyhydrochlorination of ethylene to produce EDC is begun in the manner described in the referenced Harpring et al patent using a fluid bed composed of cupric chloride supported on alumina which is prepared outside the reactor in the known manner. Bare alumina support is added to the fluid bed when there is indication that the catalyst is developing stickiness or losing its ability to fluidize, and the oxyhydrochlorination reaction is then continued whereupon cupric chloride from the already supported catalyst deposits on the bare support in situ and the stickiness is alleviated.

In another preferred embodiment of the process a mixture of bare alumina support and cupric chloride catalyst already supported on alumina is prepared by intimately mixing the two outside the reactor and then adding the mixture to the reactor. In this case, the oxyhydrochlorination of ethylene to produce EDC is effected in a fluid bed initially composed of the mixture, whereby development of stickiness during the reaction is inhibited as a portion of the cupric chloride from the supported copper catalyst deposits itself in situ on the bare support in the fluid bed as the reaction proceeds.

The bare support alone or the mixture described may also, in still other embodiments of the invention, be supplied to the operator of the oxyhydrochlorination process and used as make up when the catalyst bed needs replenishing. Here too, a portion of the cupric chloride is deposited on the bare support in situ and stickiness in the catalyst bed is alleviated.

In each of these embodiments of the invention, it is desirable but not essential that the bare alumina support used be the same alumina as that on which the cupric chloride catalyst is deposited to produce the supported catalyst.

The support used as bare support or as the support on which the cupric chloride is initially deposited is a fluidizable alumina support. The particle size of the alumina support is preferably such that 95 to 90 weight percent of the particles are below 80 microns in diameter, 40 to 50% below 45 microns in diameter and 15 to 30% below 30 microns in diameter with no more than 3 to 10% by weight of the particles smaller than 20 microns in diameter and no more than 1 to 5% larger than 200 microns in diameter. The bulk density of the preferred alumina supports is in the range of 0.8 to 1.1 grams per cc and their surface area is in the range of 60 to 150 sq. meters per gram.

Such bare alumina supports are white in color and except for a change to a greenish color, and other changes in physical characteristics as a result of cupric chloride deposits, including a 10 to 30 percent reduction in surface area, the above description of bare support is also descriptive of the cupric chloride catalyst supported on alumina with which the bare support is mixed or to which the bare support is added in the fluid bed.

The amount of bare alumina support admixed with supported cupric chloride catalyst, either prior to or after addition to the reactor, may be varied depending on the copper content of the initial supported catalyst and the desired copper content of the final supported catalyst. To achieve a significant change in the character of the fluid bed, a minimum of 5% of the weight of the entire bed should be added as bare support up to a maximum of about 50%, it being understood, however, that the limit on the maximum use of bare support is such that the final copper content, which is obviously diluted by use of bare support, is not reduced below about 2%. It should be noted, however, that the inhibition or amelioration of stickiness and improved performance of the catalyst bed effected by this invention is not due solely to reduced copper content. As will be exemplified below, a supported catalyst of a given copper content prepared in part by depositing cupric chloride on support in situ, as described, is less sticky than a catalyst of the same copper content prepared by depositing all the copper on the support before addition to the reactor.

The method of this invention is particularly useful to improve the ethylene oxyhydrochlorination process when carried out at a temperature of about 235° C. or more using a high copper content catalyst wherein the cupric chloride is supported on an alumina support having a surface area in the range of 60 to 80 square meters per gram. Operation of the process under these conditions without taking advantage of this invention can often lead to an undesirable degree of stickiness of the catalyst bed and can lead to loss of catalyst and/or hot spots in the fluid bed.

To demonstrate the extent to which use of bare support in accordance with this invention produces the desired results, it is desirable that a test method be available for determining the degree of stickiness of a given catalyst at commercial operating conditions. A test has been devised for this purpose called the Temperature Profile Test (TPT). In this test a bench-scale fluid bed reactor of 30 mm internal diameter is equipped with means for preheating and delivering a mixture of ethylene, air and HCl through a mass of supported catalyst of a given height contained in the reactor. A thermocouple is used to measure the temperature of the fluid bed at each point in its height by gradually raising the thermocouple through the height of the bed. The laboratory reactor is operated under a given sequence of operating conditions and the temperature of the bed throughout its height is noted for each specific operating condition. If the temperature varies from one point in the bed to another, for any given condition, this is an indication of stickiness and a rating, indicating stickiness, can be assigned to this supported catalyst being tested. The stickiness varies from a rating of 1 which indicates no temperature variation in any of the specific operating conditions, and hence, no stickiness, to a rating of 4 which indicates temperature variations throughout the height of the bed under each set of operating conditions and extreme stickiness. During the test, in each sequence of operating conditions, the conversion of ethylene to EDC and the yield and efficiency of EDC production can be measured so as to ascertain the effectiveness of a given supported catalyst with a determined stickiness rating in EDC production.

There is a sophisticated method and apparatus for determining the precise consistency and stickiness of an operating fluid bed and for selecting the most desirable supported catalyst among a number of catalysts (and hence, demonstrating that the supported catalyst of this invention as prepared by depositing a portion of cupric chloride on the support in situ are less sensitive and sticky than those prepared entirely outside the reactor) which is described in the copending application of Joseph A. Cowfer, et al, Ser. No. 949,170 filed Oct. 6, 1978, issued Oct. 7, 1980 as U.S. Pat. No. 4,226,798, the disclosure of which is incorporated herein by reference. As described therein in detail, the apparatus used is a laboratory fluid bed provided with a pendulum viscometer which measures the rate of damping or k value of a predetermined torsional oscillation of the pendulum during operation of the fluid bed with any given supported catalyst, and the k values as obtained for different supported catalyst can be compared to select the catalyst which is least prone to produce stickiness during the oxyhydrochlorination reaction.

The method and composition of this invention and the advantages achieved thereby, are further illustrated in the following specific examples.

EXAMPLE I

An alumina supported copper catalyst is prepared by dissolving 26.84 g. of $CuCl_2 \cdot 2H_2O$ in 110 ml. water and adding the solution in portions to 95 g of fluidizable gamma-alumina powder of the following range of particle sizes by weight: 6% below 20 microns; 15-28% less than 30 microns, 40-50% less than 45 microns and 75-91% less than 80 microns, and having a surface area of about 70 to 100 square meters per gram. The wetted alumina is evaporated to dryness on a steam bath (80° C.) until it becomes free flowing, calcined for 16 hours at 110° C. and the dry finely divided supported catalyst screened through a 20 mesh screen. The supported catalyst thus prepared is of the consistency of finely divided sand and has a greenish color. Its copper content is about 10% by weight. Its surface area is less than that of the alumina used as the support due to deposit of copper on the surfaces of the particles and is in the range of 60 to 85 square meters per gram.

A portion of this alumina supported cupric chloride catalyst is mixed thoroughly by stirring with an equal amount by weight of the same alumina support used in preparing the supported catalyst. The white particles of bare support and the greenish particles of supported catalyst are evidenced in the mixture. The percentage of copper in the mixture is now about 5% by weight.

The supported catalyst and the composition of this invention, i.e. the mixture of supported catalyst with bare support, is each separately tested in the TPT for stickiness when used as the fluid bed catalyst in the reaction of ethylene, oxygen and HCl to produce EDC. In each case, 125 l. of fluid bed material is placed in the 30 mm internal diameter fluid bed reactor to produce a bed height of 12 inches and the reactor operated by passing gaseous ethylene, oxygen (supplied as air) and HCl in a ratio of ethylene to oxygen to HCl of 1/0.8/2.0 through the bed while varying the temperature of the reaction in the fluid bed and the contact time of the gaseous reactants in the bed. In each case, any variations in temperature through the height of the bed, as well as the conversion of ethylene and the yield of EDC are measured.

Using the supported catalyst alone, at a temperature of 219° C. and a contact time of 13.1 seconds, a 66.2% conversion of ethylene is secured with approximately 66% ethylene to EDC efficiency (yield of EDC times ethylene conversion) without variation in the 219° C. temperature throughout the height of the bed. However, at higher temperatures in the range of 221° to 235° C. with contact time in the range of 14 to 22 seconds, when using the supported catalyst alone, the temperature at the bottom of the bed increased by several degrees. The catalyst became undesirably sticky as to prevent proper fluidization in the bed. This catalyst had a TPT stickiness rating of 4.

In contrast, under the same conditions, the TPT results using the equal mixture of supported catalyst and bare support shows no change in temperature throughout the height of the bed during the tests. Operating conditions used temperatures varying from 221° to 235° C. and contact times varying from 14 to 22 seconds. The ethylene conversions range from 78.4 to 97.8% and the ethylene efficiencies to EDC from 78.6 to 91.9%. This example illustrates that stickiness is inhibited. Furthermore, in this example, improved EDC efficiency was obtained by the addition of bare support to the already supported cupric chloride catalyst.

EXAMPLE II

Using the materials and procedures and conditions of Example I, alumina supported cupric chloride catalyst is prepared to contain about 5% by weight of copper. This catalyst is tested by the TPT, and a stickiness rating of 3.5 is obtained. The same catalyst is then mixed in equal proportions with the same bare alumina support used in the above preparation and the mixture tested in the TPT which gives a TPT stickiness rating of 1. This mixture, containing about 2.5% copper, was then used as the initial fluid bed in a laboratory fluid bed ethylene oxyhydrochlorination reactor of 30 MM internal diameter with a catalyst bed height of 15 inches in a run of 85 hours duration. No stickiness is observed in the entire period of observation and the bed fluidizes excellently throughout. Data for this run is shown in Table I.

TABLE I

| Temp. 0 C. | Contact Time Seconds | Hours Elapsed | Reactant Ratios | | | % Yield | | | % Efficiency |
|---|---|---|---|---|---|---|---|---|---|
| | | | $C_2H_4$ | $O_2$ | HCl | CO | $CO_2$ | EDC | EDC |
| 227 | 14.4 | 3 | 1 | 0.78 | 1.86 | 2.01 | 1.88 | 95.6 | 78.5 |
| 223 | 14.5 | 9 | 1 | 0.78 | 1.86 | 1.34 | 1.45 | 96.9 | 91.8 |
| 221 | 19.7 | 11 | 1 | 0.78 | 1.86 | 1.15 | 1.31 | 97.0 | 94.6 |
| 228 | 19.4 | 13 | 1 | 0.78 | 1.86 | 1.56 | 1.65 | 96.1 | 94.7 |
| 228 | 19.4 | 36 | 1 | 0.78 | 1.86 | 1.83 | 1.69 | 95.8 | 94.9 |
| 229 | 24.8 | 38 | 1 | 0.8 | 1.96 | 2.35 | 2.39 | 94.2 | 94.2 |
| 231 | 20.5 | 56 | 1 | 0.8 | 2.02 | 2.20 | 2.40 | 94.7 | 93.5 |
| 234 | 21.7 | 61 | 1 | 0.8 | 2.23 | 1.98 | 1.99 | 95.1 | 94.7 |
| 235 | 21 | 62 | 1 | 0.8 | 2.12 | 2.04 | 1.98 | 95.2 | 95.2 |
| 238 | 21 | 81 | 1 | 0.8 | 2.12 | 2.55 | 2.71 | 93.7 | 93.7 |
| 236 | 20 | 85 | 1 | 0.7 | 2.0 | 2.24 | 2.33 | 94.6 | 93.3 |

Catalyst Mixture Rated #1 In TPT
Supported Catalyst Is Rated #3.75 In TPT

EXAMPLE III

The materials and procedures and conditions of Example I are again repeated using various lots of alumina supported cupric chloride catalyst with various ratios of copper and various proportions of bare support. The results are shown in Table II. In the column headed "Reactor Fluid Bed Condition" the designation "sticky" corresponds to a TPT stickiness rating of 3 to 4, and the designation "fluid" corresponds to a TPT stickiness rating of 1.

TABLE II

| Supported Catalyst | | | Weight Bare Support | % Of Copper Mixture | Reactor Fluid Bed Condition |
|---|---|---|---|---|---|
| Lot | Weight | % Cu. | | | |
| A | 123 | 3.9 | 0 | — | Sticky |
| A | 123 | 3.9 | 7.2 | 3.7 | Fluid |
| B | 124 | 5.0 | 0 | — | Sticky |
| B | 74.5 | 5.0 | 74.5 | 2.5 | Fluid |
| C | 116 | 5.0 | 0 | — | Sticky |
| C | 85 | 5.0 | 56.7 | 3.0 | Fluid |
| C | 65 | 5.0 | 65 | 2.5 | Fluid |

EXAMPLE IV

In this Example, a cupric chloride on alumina supported catalyst is prepared as described in Example I entirely outside the reactor. The catalyst contains 3.75% copper and is tested in the TPT procedure. It has a rating of 3.0. In contrast, a mixture of copper on alumina catalyst containing 5% copper and bare alumina is prepared to give an overall copper content of 3.75%. This mixture is similarly tested and found to have a rating of 1 in the TPT procedure. This Example clearly indicates that the inhibition of stickiness is not due solely to a reduction in overall copper content, and that the deposit of a portion of the copper on the bare support is advantageous in inhibiting the development of stickiness in the fluid bed.

We claim:

1. In the production of ethylene dichloride by fluid bed catalytic oxyhydrochlorination of ethylene by a process which includes the steps of:
   (1) introducing only gaseous reactants consisting of ethylene, hydrogen chloride gas and an oxygen-containing gas in a molar ratio of 1.0 to 1.2 moles of ethylene and 0.55 to 0.9 moles of oxygen for each 2 moles of hydrogen chloride into a bed of solid particles contained in a reaction zone at a flow rate such as to fluidize said solid particles and form a fluidized catalyst bed, said catalyst bed consisting of solid particles of a fluidizable alumina support having a surface area in the range of 60 to 150 square meters per gram, on which have been deposited outside said reaction zone catalytic salt consisting of cupric chloride in an amount such that the particles making up the bed contain 2 to about 10 weight percent copper,
   (2) maintaining said gaseous reactants in said reaction zone in contact with said fluidized solid particles under conditions such there is complete lack of liquid in said reaction zone and vapor phase reaction occurs to produce ethylene chloride, said reaction conditions including a temperature in the range of 190° to 250° C. and a contact time for any given quantity of reactants, of 10 to 40 seconds, and
   (3) recovering ethylene dichloride from the gaseous effluent from said reaction zone, the improvement for substantially preventing particles in said catalyst bed from sticking to one another during said process and thereby adversely affecting the ability to maintain the catalyst bed in the fluidized condition, which improvement consists in providing in the reaction zone to the fluidized bed of step (1), bare solid particles of said fluidizable alumina support on which no catalyst has been deposited and in situ in step (2) transferring to and depositing on said bare support particles a portion of the cupric chloride catalyst already deposited outside the reaction zone on other fluidizable support particles.

2. The process improvement of claim 1 further characterized in that the particles of fluidizable alumina support having surface area in the range of 60 to 150 square meters per gram additionally have a particle size distribution such that 90 to 95 weight percent of said particles are below 80 microns in diameter, 40 to 50 weight percent thereof are below 80 microns in diameter, 15 to 30 percent thereof are below 30 microns in diameter, no more than 3 to 10 weight percent thereof are smaller than 20 microns in diameter and no more than 1 to 5 weight percent thereof are larger than 200 microns in diameter.

3. The process improvement of claim 2 further characterized in that the proportion of bare particles of fluidizable alumina support so provided to the reaction zone is from 5 to 50 weight percent of the total of said bare particles plus the particles on which cupric chloride is already deposited outside the reaction zone.

4. The process improvement of claim 3 further characterized in that the reactants in the reaction zone are maintained at a temperature of 235° to 250° C., the fluidizable alumina support particles have a surface area in the range of 60 to 80 square meters per gram and the copper content of the support on which cupric chloride is deposited outside the reaction zone is about 5 weight percent.

* * * * *

UNITED STATES PATENT AND TRADEMARK OFFICE
CERTIFICATE OF CORRECTION

PATENT NO. : 4,339,620

DATED : July 13, 1982

INVENTOR(S) : Joseph Allen Cowfer, Jamal Shahab Eden, Angelo Joseph Magistro

It is certified that error appears in the above-identified patent and that said Letters Patent are hereby corrected as shown below:

In Column 8, line 63, in Claim 2, line 7 thereof, delete the number "80" and add the number ---45---.

Signed and Sealed this

Sixteenth Day of November 1982

[SEAL]

Attest:

GERALD J. MOSSINGHOFF

Attesting Officer    Commissioner of Patents and Trademarks